(12) United States Patent
Toida (10) Patent No.: US 6,542,245 B2
(45) Date of Patent: Apr. 1, 2003

(54) DYNAMIC CHANGE DETECTING METHOD, DYNAMIC CHANGE DETECTING APPARATUS AND ULTRASONIC DIAGNOSTIC APPARATUS

(75) Inventor: Masahiro Toida, Kawasaki (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 37 days.

(21) Appl. No.: 09/843,772

(22) Filed: Apr. 30, 2001

(65) Prior Publication Data

US 2001/0046052 A1 Nov. 29, 2001

(30) Foreign Application Priority Data

May 2, 2000 (JP) .................................. 2000-133086

(51) Int. Cl.[7] ................................................ G01B 9/02
(52) U.S. Cl. ...................................... 356/480; 356/432
(58) Field of Search ............................... 356/432, 477, 356/480, 502

(56) References Cited

U.S. PATENT DOCUMENTS

| 4,581,939 A | * | 4/1986 | Takahashi | 73/643 |
| 4,633,715 A | * | 1/1987 | Monhalin | 75/657 |
| 5,585,921 A | * | 12/1996 | Pepper et al. | 356/357 |
| 5,684,592 A | * | 11/1997 | Mitchell et al. | 356/357 |

OTHER PUBLICATIONS

E.D. Light et al "Progress in Two–Dimensional Arrays for Real–Time Volumetric Imaging UltrasonicImaging" 20, 1–15 (1998).

Takahashi et al, "Underwater Acoustic Sensor With Fiber Bragg Grating Optical Review", vol. 4, No. 6 (1997) 6911–694.

Uno et al, Fabrication and Performance of a Fiber Optic Micro–Probe for Megahertz Ultrasonic Field Measurement T. IEEE Japan, vol. 118–E, No. 11, 1998.

* cited by examiner

Primary Examiner—Stephone Allen
(74) Attorney, Agent, or Firm—Sughrue Mion, PLLC (57) ABSTRACT

A dynamic change detecting apparatus permits selection of a combination condition of various detection sensitivities and dynamic ranges. This apparatus has a light source for emitting light having at least one wavelength component; a detecting element having a detecting part composed by connecting a resonant part including a medium having a predetermined thickness and a total reflection mirror to one end of a transmission/reflection part having transmission/reflection properties varying with a wavelength of incident light, the light emitted by the light source being entered from the other end of the transmission/reflection part into the detecting element; a plurality of light detectors for detecting the light reflected by the detecting part to detect a detection signal; and a signal processing unit for detecting dynamic change propagating to the total reflection mirror on the basis of change in amplitude of the detection signal corresponding to change in size of the detecting part caused by propagation of the dynamic change.

20 Claims, 11 Drawing Sheets

REFLECTION PROPERTY OF
TRANSMISSION/REFLECTION PART

EMISSION SPECTRUM OF SLD

DYNAMIC CHANGE DETECTING METHOD, DYNAMIC CHANGE DETECTING APPARATUS AND ULTRASONIC DIAGNOSTIC APPARATUS

BACKGROUND OF THE INVENTION

1. Field of the Invention

The present invention relates to a method and an apparatus for detecting a dynamic change in ultrasonic wave or the like propagating through a medium. Furthermore, the invention relates to an ultrasonic diagnostic apparatus having such a dynamic change detecting apparatus.

2. Description of a Related Art

In an ultrasonic diagnostic apparatus for so-called ultrasonic echo observation or the like, it is the general practice to use a piezo-electric material typically represented by PZT (Pb (lead) titanate zirconate) for an ultrasonic sensor section (probe).

Figure 11A:
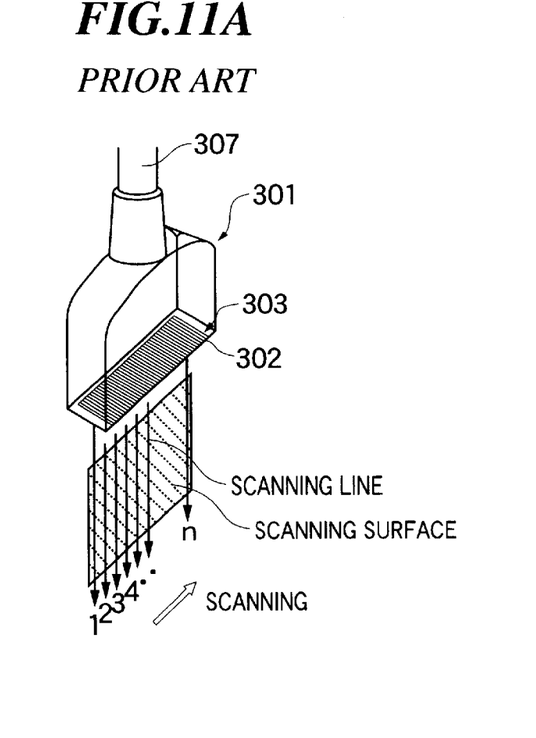
FIG. 11A is a perspective view illustrating a whole structure of a conventional probe.
Figure 11B:
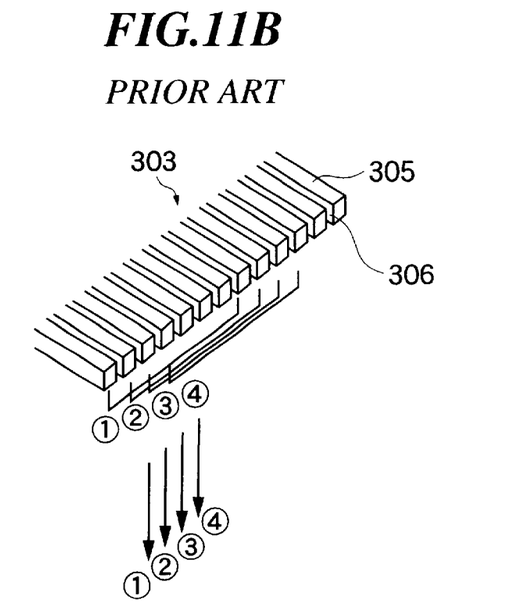
FIG. 11B is an enlarged perspective view illustrating an array oscillator contained in the conventional probe.

FIGS. 11A and 11B schematically illustrate the structure of a conventional probe: FIG. 11A is a whole perspective view of the probe, and FIG. 11B is an enlarged perspective view illustrating an array oscillator.

The probe 301 has a thin box shape as a whole and has a long and slender rectangular probing surface 302. This probing surface 302 is brought into contact with a human body and an ultrasonic wave is radiated so as to receive an ultrasonic echo reflected from the depth of the body. In FIG. 11A, a cable 307 sending an ultrasonic receiving signal is connected to the upper side of the probe 301.

A comb-shaped array oscillator 303 serving simultaneously as a transmitter and a receiver of ultrasonic wave is housed in the probing surface 302. The array oscillator 303 is formed by providing a number of slits 306 (having a width of, for example, 0.1 mm) in a thin (having a thickness of, for example, 0.2 to 0.3 mm) strip-shaped PZT sheet and arranging many (for example, 256) comb-teeth-shaped individual oscillators 305 (having, for example, a width of 0.2 mm and a length of 20 mm).

Electrodes are formed in each individual oscillator 305, and signal lines are connected thereto. An acoustic lens layer or an acoustic matching layer made of a resin material such as rubber is pasted to the surface side (lower side in FIG. 11A) of the array oscillator 303, and a packing material is pasted onto the back side. The acoustic lens layer converges the transmitted ultrasonic waves effectively. The acoustic matching layer improves the transmission efficiency of ultrasonic waves. The packing material has a function of holding the oscillator and causes oscillation of the oscillator to be finished early.

These ultrasonic probes and ultrasonic diagnostic apparatuses are described in detail in the "Ultrasonic Observing Method and Diagnostic Method", Toyo Publishing Co., and "Fundamental Ultrasonic Medicine", Ishiyaku Publishing Co.

In the area of ultrasonic diagnosis, collection of three-dimensional data is demanded for obtaining more detailed information about the interior of an object's body. In order to comply with such a demand, it is required to make ultrasonic detecting elements (ultrasonic sensors) into a two-dimensional array. In the aforementioned PZT, however, refinement and integration of devices over the present status is difficult for the following reasons. That is, the processing technology of PZT materials (ceramics) is on a limit level, and further refinement leads to an extreme decrease in processing yield. This furthermore results in an increase in the number of wires, thus leading to an increase in electrical impedance of wiring. In addition, there is an increase in crosstalk between individual elements (individual oscillators). It is therefore considered difficult at the present level of art to achieve a two-dimensional array probe using a PZT.

A paper entitled "Progress in Two-Dimensional Arrays for Real-Time Volumetric Imaging" by E. D. Light et al., Duke University, appears in ULTRASONIC IMAGING 20, 1–15 (1998), disclosing a probe having a two-dimensional array of PZT ultrasonic sensors. The paper however states "In order to obtain an image of a similar quality, it is necessary to provide 128×128=16,384 elements of the two-dimensional array. However, it is complicated and expensive to make such many RF channels, and therefore, there is only a little chance of this solution in the future. It is furthermore very difficult to densely connect such many elements." (page 2, lines 14–18).

On the other hand, a sensor using optical fibers is used as an ultrasonic sensor not using a piezo-electric material such as PZT. Such an optical-fiber ultrasonic sensor is suitable for measurement at a location largely affected by magnetic field or at a narrow site.

There is available a kind of optical fiber ultrasonic sensor which uses an optical fiber Bragg grating (hereinafter abbreviated as an "FBG") (see TAKAHASHI, National Defense Academy, et al. "Underwater Acoustic Sensor with Fiber Bragg Grating" OPTICAL REVIEW, Vol. 4, No. 6 (1997) 691–694). An FBG is formed by alternately laminating two kinds of material layers (light propagating medium) having different values of refractive index in several thousand layers so that refractive index changes periodically at a pitch satisfying Bragg's reflection conditions. The pitch of the periodic structure is $\Delta$, a wavelength of incident light is $\lambda$, and N is an arbitrary integer, then, Bragg's reflecting condition is expressed by the following formula:

$$2N\Delta=\lambda$$

Under the action of Bragg reflection, the FBG selectively reflects light having a particular wavelength satisfying the above formula, and causes light having the other wavelengths to pass through.

When an ultrasonic wave is caused to propagate to FBG, the wavelength $\lambda$ of the light selectively reflected changes because deformation of FBG leads to change in the pitch $\Delta$ of the aforementioned periodic structure. In practice, there are slant zones in which the reflectance varies before and after a central wavelength showing the highest reflectance (lowest transmittance), and an ultrasonic wave is applied to the FBG while a detection light having a wavelength in these slant zones is made incident to the FGB. It is thus possible to observe change in intensity of the reflected light (or transmitting light) corresponding to intensity of the ultrasonic wave. The ultrasonic intensity can be determined by converting this change in light intensity into an electric signal.

There is available another kind of optical fiber ultrasonic sensor using a Fabry-Perot resonator (hereinafter abbreviated as an "FPR") (see UNO et al., Tokyo Institute of Technology, "Fabrication and Performance of a Fiber optic Micro-Probe for Megahertz Ultrasonic Field Measurements", T. IEE Japan, Vol. 118-E, No. 11, '98).

The sensor of UNO et al. is prepared by forming a half mirror through vapor deposition of gold at the leading end of a single-mode optical fiber ($\lambda=1.3$ μm, core: 10 μm and clad: 125 μm), providing a cavity (length: 100 μm) by a member of polyester resin (n=1.55) at the leading end thereof, and forming a total reflection mirror by gold vapor deposition further at the leading end thereof.

Detection light having a wavelength λ is made incident into this sensor from the half mirror side, and an ultrasonic wave is transmitted from the total reflection side. When the reflectance of the half mirror is r, the single pass gain is G, the length of the cavity is L, and the refractive index is n, then, the reflectance R of this sensor is determinable from the following formula:

$$R = \frac{(\sqrt{r} - G)^2 + 4\sqrt{r}\,G\sin^2\delta}{(1 - \sqrt{r}\,G)^2 + 4\sqrt{r}\,G\sin^2\delta}$$

where, δ is calculated by means of the following formula:

$$\delta = 2\pi L n/\lambda$$

The formula expressing δ suggests that change in an optical path length 2L of a reciprocation of the cavity caused by change in sound pressure of the ultrasonic wave, i.e., change in the optical path length L leads to change in the reflection property of the light from the sensor.

In practice, there are slant zones in which the reflectance varies before and after the central wavelength giving the lowest reflectance, and change in intensity of the reflected light corresponding to the intensity of ultrasonic wave can be observed by applying an ultrasonic wave to the FPR while the detection light of any of the slant zones into the FPR is made incident. The intensity of ultrasonic wave can be determined by converting this change in intensity of the light.

The aforementioned ultrasonic sensor using optical fiber has however a defect. If steep characteristics of the slant zones are designed with a view to improving the detection sensitivity, the dynamic range becomes inevitably narrower. Design of slower characteristics in contrast results in a wider dynamic range, but in poorer detection sensitivity.

SUMMARY OF THE INVENTION

The present invention was developed in view of these problems. The invention has a first object to permit, in the detection of a dynamic change, selection of various combination conditions of detection sensitivity and dynamic range. A second object of the invention is to make it possible to detect a dynamic change in parallel under a plurality of combination conditions.

For the purpose of solving these problems, the dynamic change detecting method according to the present invention comprises the steps of: (a) entering light having at least one wavelength component from one end of a transmission/reflection part having transmission/reflection properties varying with a wavelength of incident light into a detecting element having a detecting part composed by connecting a resonant part including a medium having a predetermined thickness and a total reflection mirror to the other end of the transmission/reflection part; (b) detecting the reflected light by means of the detecting part to obtain a detection signal; and (c) detecting dynamic change propagating to the total reflection mirror, on the basis of change in amplitude of the detection signal corresponding to change in size of the detecting part caused by propagation of the dynamic change.

The dynamic change detecting apparatus according to the present invention comprises a light source for emitting a light having at least one wavelength component; a detecting element having a detecting part composed by connecting a resonant part including a medium having a predetermined thickness and a total reflection mirror to one end of a transmission/reflection part having transmission/reflection properties varying with a wavelength of incident light, light emitted by the light source being entered from the other end of the transmission/reflection part into the detecting element; a plurality of light detectors for detecting the light reflected by the detecting part to detect a detection signal; and a signal processing unit for detecting dynamic change propagating to the total reflection mirror, on the basis of change in amplitude of the detection signal corresponding to change in size of the detecting part caused by propagation of the dynamic change.

The ultrasonic diagnostic apparatus according to the present invention comprises a transmitting unit for transmitting an ultrasonic wave to an object; a light source for emitting a light having at least one wavelength component; a detecting element having a detecting part composed by connecting a resonant part including a medium having a predetermined thickness and a total reflection mirror to one end of a transmission/reflection part having different transmission/reflection properties in response to a wavelength of incident light, the light emitted by the light source being entered from the other end of the transmission/reflection part to the detecting element; a plurality of light detectors for detecting the light reflected by the detecting part to obtain a detection signal; a signal processing unit for detecting dynamic change propagating to the total reflection mirror, on the basis of change in amplitude of the detection signal corresponding to change in size of the detecting part caused by propagation of the dynamic change; and an image display unit for displaying an image on the basis of the signal output from the signal processing unit.

According to the invention, there is used a detection element having a detecting part formed by connecting a resonant part including a medium having a predetermined thickness and a total reflection mirror to one end of a transmission/reflection part 3 having transmission/reflection properties varying with a wavelength of incident light. It is therefore possible to achieve simultaneously high detection sensitivity and a wide dynamic range by changing the wavelength of the incident light.

DESCRIPTION OF THE PREFERRED EMBODIMENTS

Embodiments of the present invention will now be described in detail with reference to the drawings. The same reference numerals are assigned to the same component elements, and the description thereof is omitted.

Figure 1A:
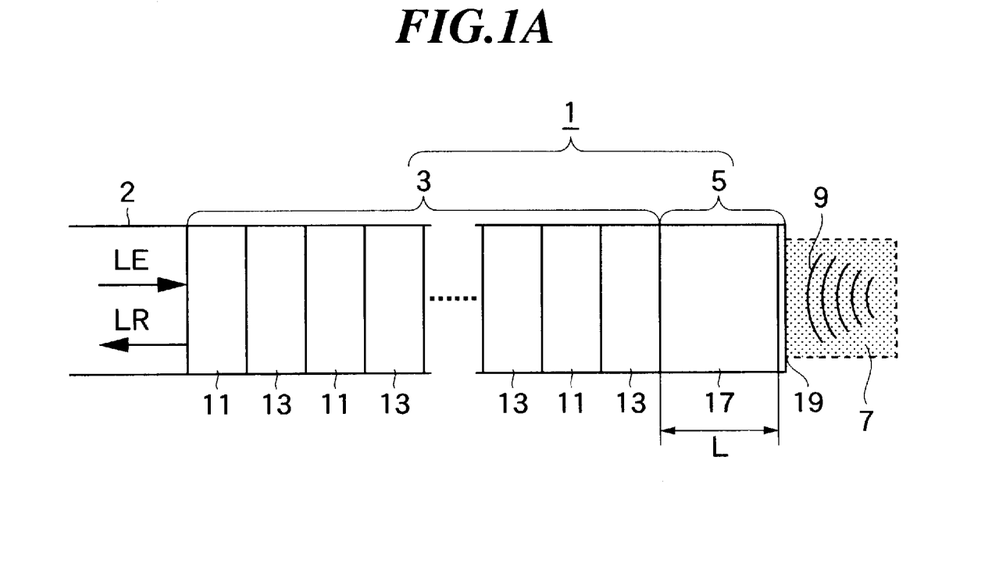
FIG. 1A is a sectional view of a detection element (sensor) contained in a dynamic change detecting apparatus according to a first embodiment of the present invention.
Figure 1B:
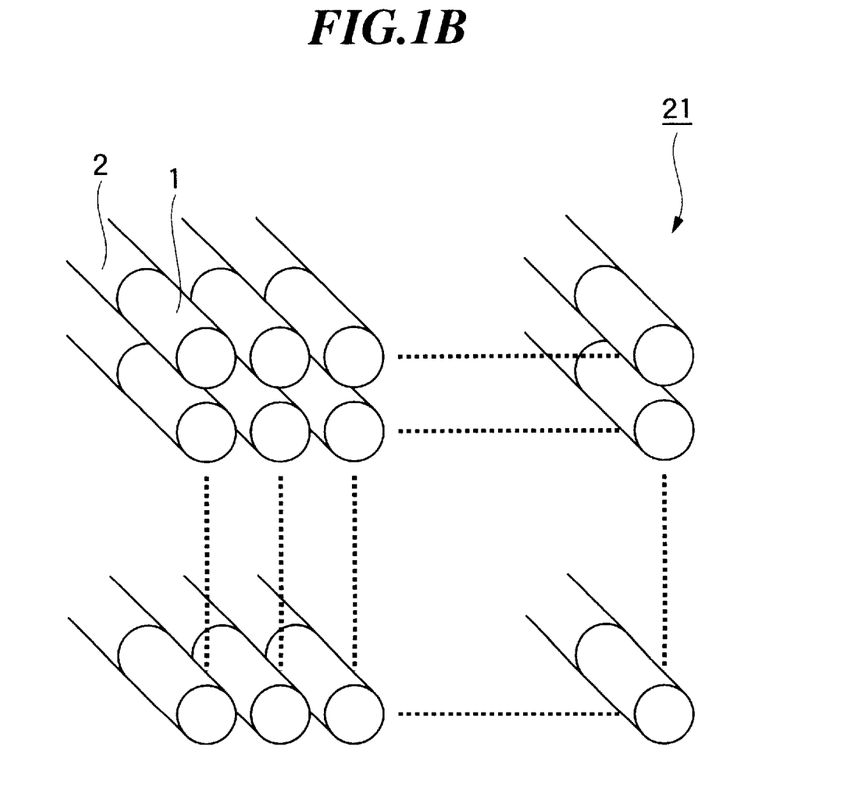
FIG. 1B is a perspective view illustrating arrangement of many detection elements in a two-dimensional array, contained in the dynamic change detecting apparatus according to the first embodiment of the invention.

FIGS. 1A and 1B schematically represent a detection element (ultrasonic sensor) contained in a dynamic change detecting apparatus according to a first embodiment of the invention: FIG. 1A is a sectional view of one detection element; and FIG. 1B is a perspective view showing arrangement of a plurality of detection elements in a two-dimensional array.

The detection element includes an optical fiber 2 and a detecting part 1 formed at the leading end of the optical fiber 2. The detecting part 1 has a transmission/reflection part 3 connected to the leading end of the optical fiber 2, and a resonant part 5 connected to the transmission/reflection part 3. The transmission/reflection part 3 forms an optical fiber Bragg grating (FBG), and the resonant part 5 forms a Fabry-Perot resonator (FPR). Therefore, an optical fiber Bragg grating type Fabry-Perot interference system is composed of the transmission/reflection part 3 and the resonant part 5.

Detection light LE enters from the optical fiber 2 into the detecting part 1, and on the contrary, the reflected light LR enters from the detecting part 1 into the optical fiber 2. The total reflection mirror 19 of the resonant part 5 arranged at the leading end of the detecting part 1 is in contact with an object 7, and an ultrasonic wave 9 propagating through the object 7 is applied. In this detection element, the optical path length is varied by causing deflection of the resonant part 5 by causing propagation of dynamic change from the total reflection mirror 19 side to the resonant part 5. The propagated dynamic change can be detected from change in reflection properties resulting from this change in optical path length. Because transmittance/reflectance of the transmission/reflection part 3 can be varied by changing a wavelength of incident light, it is possible to cause change in detection sensitivity of the detecting part 1.

The transmission/reflection part (FBG) 3 is formed by alternately laminating two kinds of material layers having different values of refractive index in several thousand layers so that the refractive index periodically changes at a pitch satisfying Bragg's reflection condition (for example, 0.5 μm) (see APPLIED PHYSICS, Vol. 67, No. 9 (1998), p. 1029). When the pitch of the periodic structure of each layer is Δ, the wavelength of the incident light is λ, and N is an arbitrary integer, Bragg's reflection condition would be as follows:

$$2N\Delta = \lambda$$

This FBG selectively reflects light having a specific wavelength satisfying the condition of the above-mentioned formula in accordance with Bragg's reflection condition, and causes light having the other wavelengths to pass through.

The resonant part 5 includes a light transmissive medium 17 connected to the transmission/reflection part 3 and a total reflection mirror 19 formed at the leading end thereof. The transmission/reflection part 3 is considered as a half mirror and is assumed to be present at an end of the medium 17.

The detection light of a wavelength λ is entered from the transmission/reflection part 3 side into the resonant part 5, and an ultrasonic wave is applied from the total reflection mirror side. When the reflectance of the half mirror is r, the single-path gain is G, the length of the medium 17 is L, and the refractive index of the medium 17 is n, then, the reflectance R of the resonant part 5 is given by the following formula:

$$R = \frac{(\sqrt{r} - G)^2 + 4\sqrt{r}\,G\sin^2\delta}{(1 - \sqrt{r}\,G)^2 + 4\sqrt{r}\,G\sin^2\delta}$$

where, δ is calculable from:

$$\delta = 2\pi L n/\lambda$$

This formula suggests that change in the optical path length 2L of a reciprocation of the medium 17 caused by change in sound pressure of ultrasonic wave results in change in the reflection property of the light from the resonant part 5.

In practice, there are slant zones in which the reflectance varies before and after a central wavelength showing the lowest reflectance, and change in intensity of the reflected light corresponding to the intensity of ultrasonic wave can be observed by applying the ultrasonic wave to the FPR while the detection light of any of the slant zones is made incident into the FPR. The ultrasonic intensity can be determined by converting this change in light intensity.

As shown in FIG. 1B, the two-dimensional array ultrasonic sensor 21 is formed by arranging a plurality of detection elements longitudinally and transversely in a matrix shape.

Figure 2:
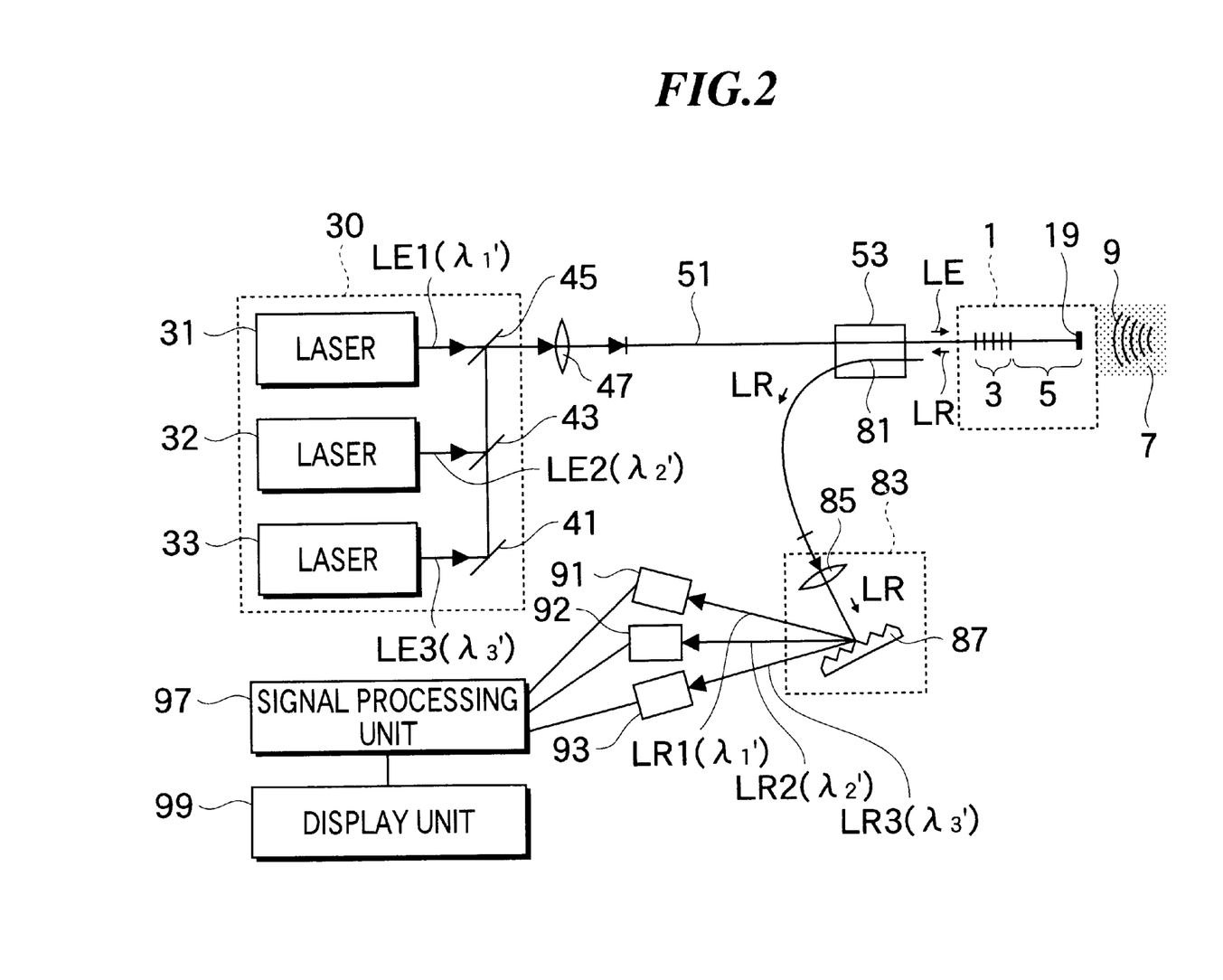
FIG. 2 illustrates a configuration of the dynamic change detecting apparatus according to the first embodiment of the invention.

FIG. 2 illustrates a configuration of the dynamic change detecting apparatus (ultrasonic detecting apparatus) of this embodiment.

A detecting part 1 similar to that as shown in FIG. 1 is shown on the right side in FIG. 2, and an optical fiber 51 having this detecting part 1 formed therein extends to the left side in FIG. 2.

In FIG. 2, a light source unit 30 is shown on the left side of the optical fiber 51. The light source unit 30 has three lasers 31, 32 and 33. The laser 31 emits a laser beam LE1 having a wavelength $\lambda_1$'; the laser 32 emits a laser beam LE2 having a wavelength $\lambda_2$'; and the laser 33 emits a laser beam LE3 having a wavelength $\lambda_3$'.

A mirror 41 is arranged diagonally upward on the emitting side of the laser 33, and the laser beam LE3 is reflected upward. A dichroic mirror 43 is arranged diagonally upward on the emitting side of the laser 32, and the laser beam LE2 is reflected upward. The laser beam LE3 passes, on the other hand, through the dichroic mirror 43. Another dichroic mirror 45 is arranged diagonally upward also on the emitting side of the laser 31. The laser beam LE1 transmits the dichroic mirror 45. On the other hand, the laser beam LE2 and the laser beam LE3 are reflected by the dichroic 45. In summary, the three laser beams LE1, LE2 and LE3 are combined at the dichroic mirror 45 and go to the right.

A lens 47 is arranged on the right side of the dichroic mirror 45. The combined light is converged through this lens 47 and enters the optical fiber 51. The optical fiber 51 extends to the right side through an optical coupler 53. The detecting part 1 having the transmission/reflection part 3 and the resonant part 5 described above with reference to FIG. 1 is connected to the leading end of the optical fiber 51.

The reflected light LR enters from the detecting part 1 into the optical fiber 51. The reflected light LR enters the optical fiber 81 at the optical coupler 53. The optical fiber 81 extends downward, and a light separating unit 83 is provided ahead of it. The light separating unit 83 has a lens 85 and a diffraction grating 87. The lens 85 is provided on the exit side of the optical fiber 81, and causes the light LR emitted from the optical fiber 81 to converge and direct to the diffraction grating 87. After directing to the diffraction grating 87, the light LR is separated into light LR1, light LR2 and light LR3 having different diffraction angles for individual wavelength components and runs to the left side.

Three light detectors 91, 92 and 93 are arranged on the left side of the light separating unit 83. The light detectors 91 to 93 receive light LR1 (wavelength: $\lambda_2'$), LR2 (wavelength: $\lambda_2'$) and LR3 (wavelength: $\lambda_3'$) separated by the light separating unit 83, and detect the respective intensities thereof. Each of the light detectors 91 to 93 sends the detected intensity of light as an electric signal to the signal processing unit 97. The signal processing unit 97 processes the received signal to obtain an image signal and sends the image signal to the display unit 99. For particulars regarding general signal processing in this field, refer to "Ultrasonic Observation Method and Diagnostic Method", Toyo Publishing Co., or "Fundamental Ultrasonic Medicine", Ishiyaku Publishing Co.

Figure 3:
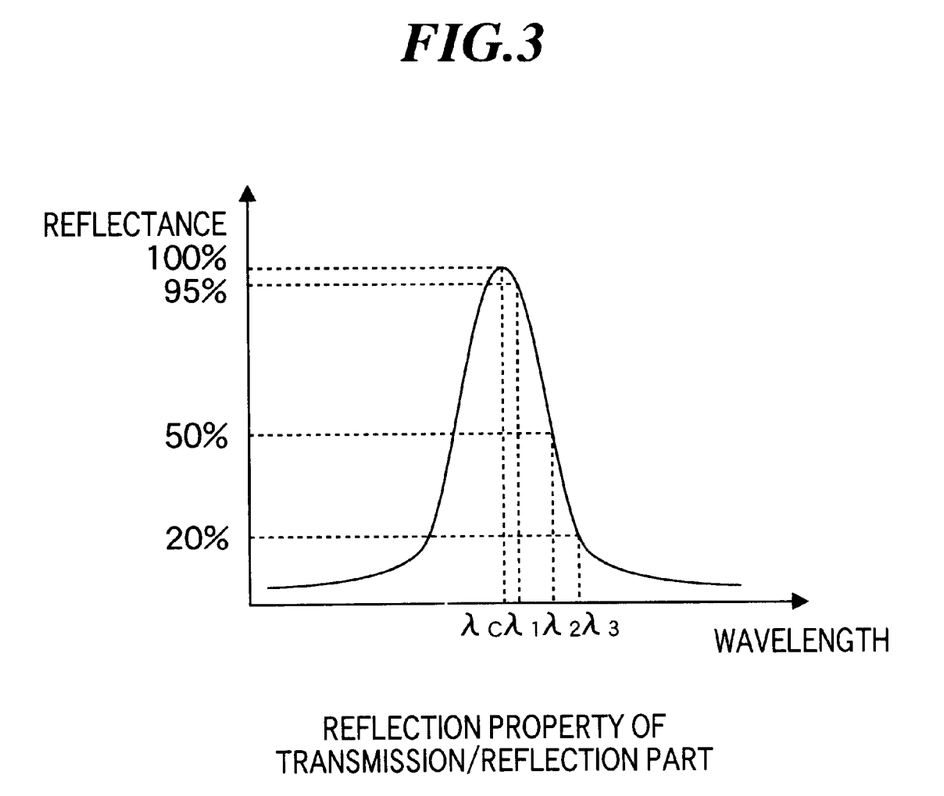
FIG. 3 illustrates reflection property of the transmission/reflection part in the first embodiment of the invention.

FIG. 3 illustrates reflection property of the transmission/reflection part (FBG) 3: the vertical axis represents the reflectance, and the horizontal axis represents the wavelength. A peak of the reflectance is shown in FIG. 3. The central wavelength of this peak is represented by $\lambda c$; the wavelength with a reflectance of 95% slightly outside this peak is $\lambda_1$; the wavelength substantially at the center (reflectance: 50%) of the slope (slant zone) on the right of the peak is $\lambda_2$; and the wavelength at the portion under the slope (reflectance: 20%) is $\lambda_3$.

Figure 4A:
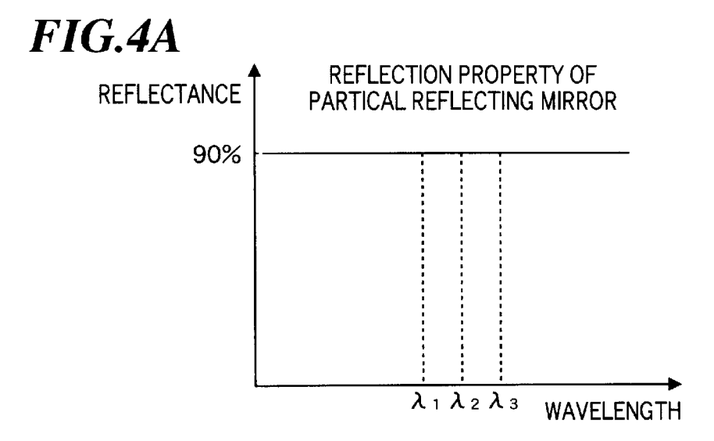
FIGS. 4A to 4C illustrate reflection properties of various parts when the half mirror has a reflectance of 90% in the first embodiment of the invention.
Figure 4B:
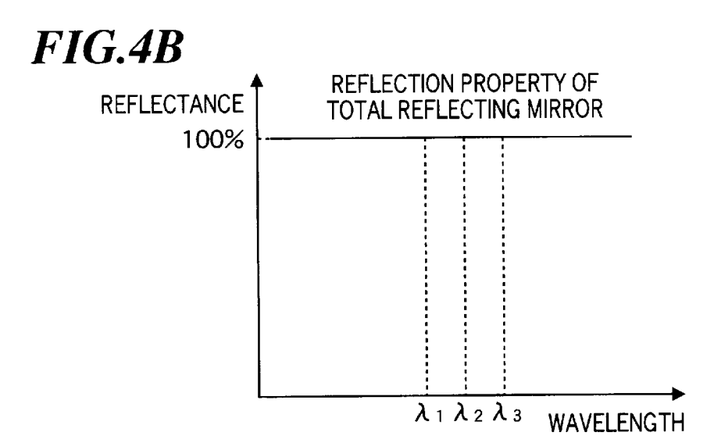
Figure 4C:
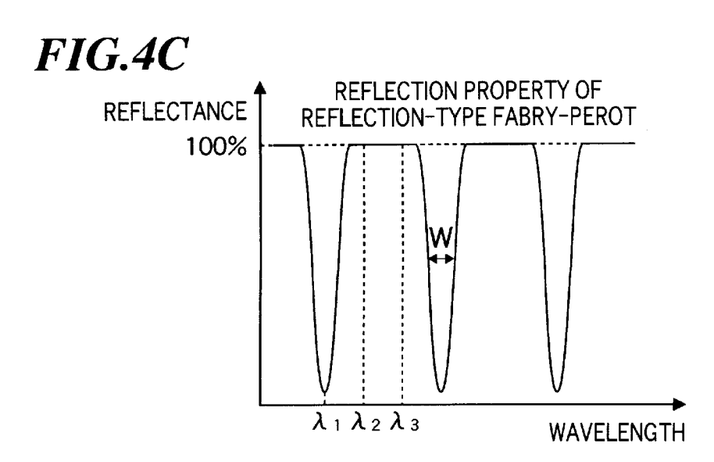
Figure 5A:
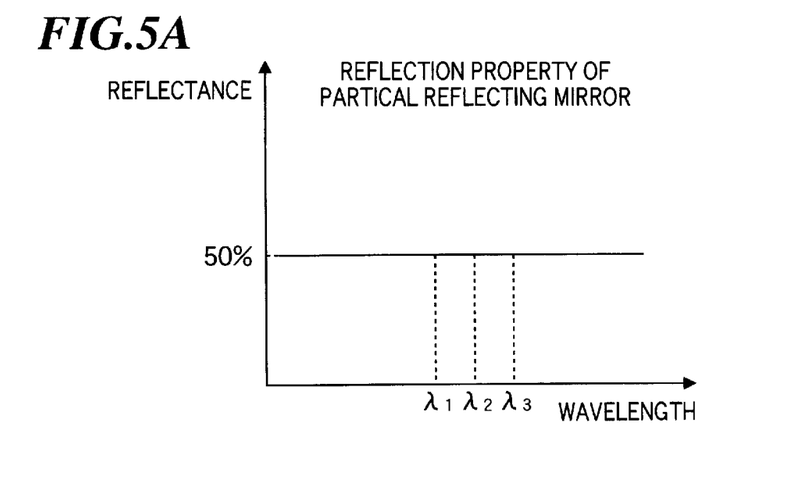
FIGS. 5A to 5C illustrate reflection properties of various parts when the half mirror has a reflectance of 50% in the first embodiment of the invention.
Figure 5B:
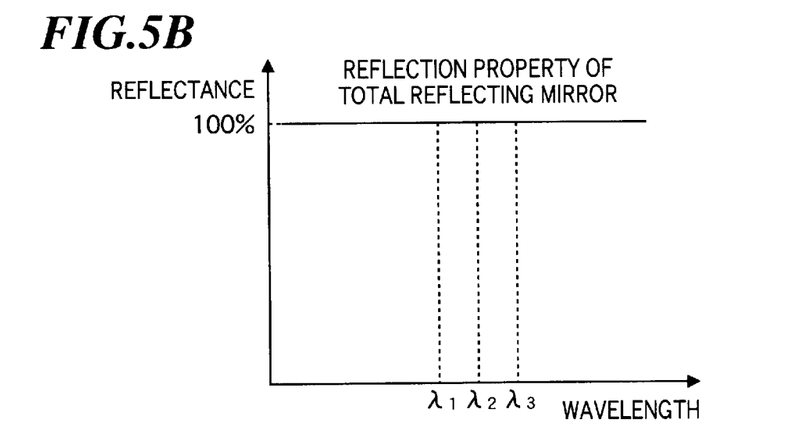
Figure 5C:
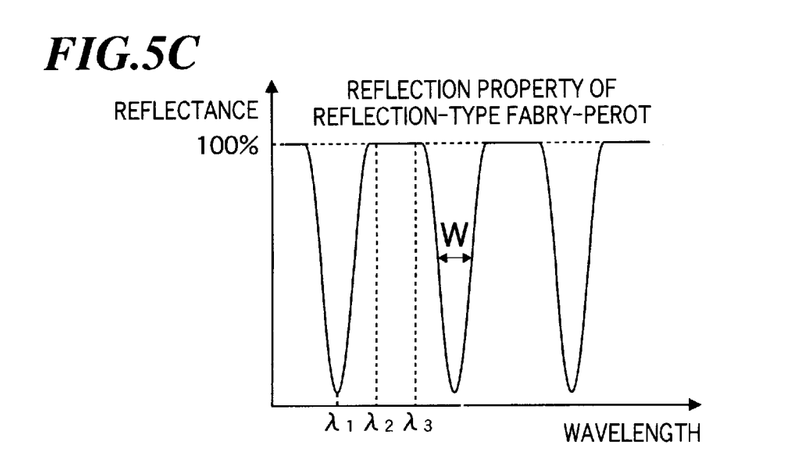
Figure 6A:
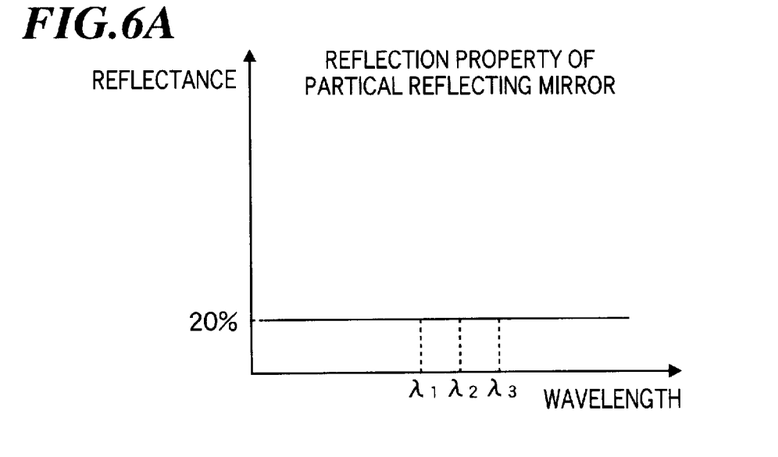
FIGS. 6A to 6C illustrate reflection properties of various parts when the half mirror has a reflectance of 20% in the first embodiment of the invention.
Figure 6B:
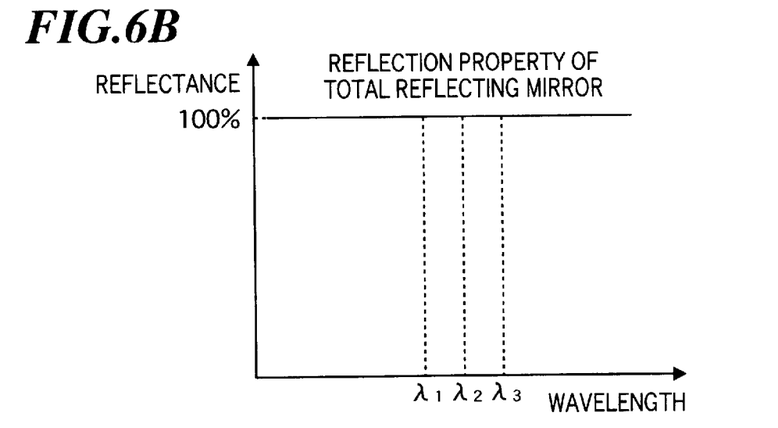
Figure 6C:
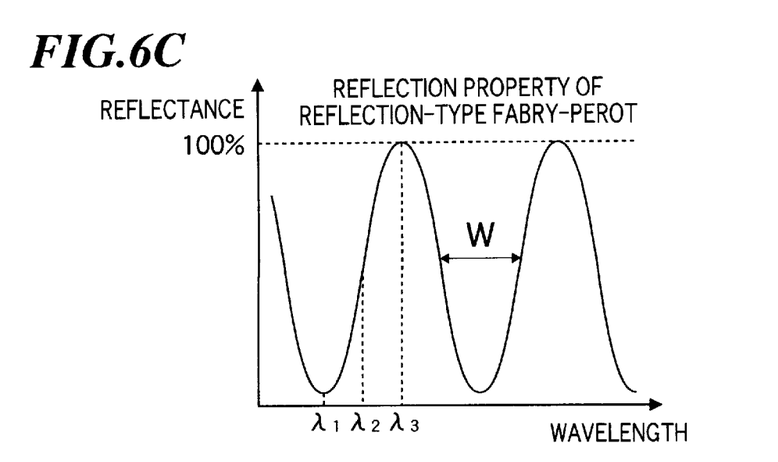

FIGS. 4A to 6C are descriptive views of the reflection properties of the resonant part 5 (FPR). Among others, FIGS. 4A to 4C are views for explaining reflection property when the half mirror has a reflectance of 90%. FIGS. 5A to 5C are views for explaining reflection properties when the half mirror has a reflectance of 50%. FIGS. 6A to 6C are views for explaining reflection properties when the half mirror has a reflectance of 20%. The vertical axis represents the reflectance, and the horizontal axis represents the wavelength.

As shown in FIGS. 4B, 5B and 6B, the total reflection mirror has a reflectance of substantially 100% (total reflection) for all the above-mentioned wavelengths $\lambda_1$, $\lambda_2$ and $\lambda_3$. As shown in FIGS. 4C, 5C and 6C, a minimum reflectance appears periodically, and a higher reflectance in reflection property of partial reflection mirror leads to a narrower half band width W of concave portions of reflectance in reflection property of the reflection type Fabry-Perot.

The reflection property of the detecting part 1 as shown in FIG. 1 results from the reflection property of the transmission/reflection part 3, the reflection property of the resonant part 5, and the resonance property between the transmission/reflection part 3 and the resonant part 5. The property can be expressed by the following formula:

$$G_R = \frac{(\sqrt{R} - G_S)^2 + 4\sqrt{R}\, G_S \sin^2(2\pi n L/\lambda)}{(1 - \sqrt{R}\, G_S)^2 + 4\sqrt{R}\, G_S \sin^2(2\pi n L/\lambda)}$$

where, $G_R$ represents the reflectance of the detecting part as a whole; R, the reflectance of the partial reflection mirror; and $G_S$, the gain of the resonant part 5.

Figure 7:
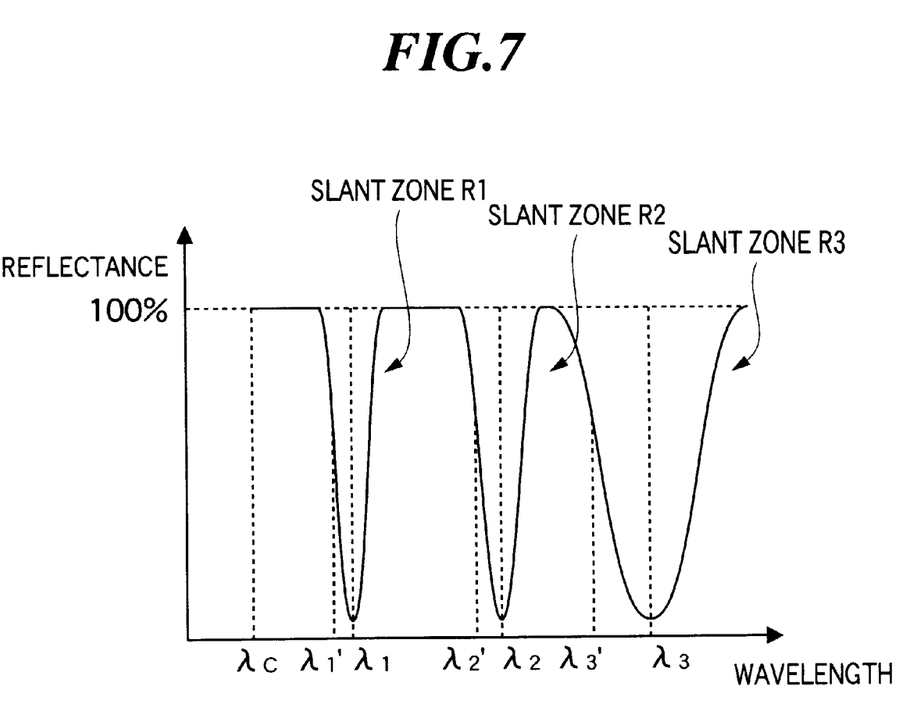
FIG. 7 illustrates reflection properties of the detecting part in the first embodiment of the invention.

FIG. 7 illustrates the reflection property of the detecting part: the vertical axis represents the reflectance, and the horizontal axis represents the wavelength. Three concave portions of a low reflection property are shown in FIG. 7. The left concave portion is called as the slant zone R1, the center concave portion, the slant zone R2, and the right concave portion, the slant zone R3. The central wavelengths of the concave portions are designed as $\lambda_1$, $\lambda_2$ and $\lambda_3$, respectively, due to the reflection property of the transmission/reflection part.

Laser wavelengths $\lambda_1'$, $\lambda_2'$ and $\lambda_3'$ of the light used for detecting a dynamic change are set within the slant zone of the individual reflection properties shown in FIG. 7. For example, $\lambda_1'$ is set in the slant zone R1. When ultrasonic wave is entered into the total reflection film surface of the resonator, a slight displacement is caused in the total reflection film surface, and a slight change occurs in the resonator length of the Fabry-Perot resonator. The slant zone R1 of the reflection property as shown in FIG. 7, therefore, shifts in the wavelength axis (horizontal axis) direction. As a result, the reflectance for the wavelength $\lambda_1'$ changes and hence the optical intensity of the wavelength $\lambda_1'$ coming back from the Fabry-Perot resonator changes, thus permitting detection of ultrasonic wave.

In order to improve sensitivity of ultrasonic detection, the minimum reflectance is reduced and the half band width of the concave portion of the reflection property is reduced so as to increase change in optical intensity and to achieve a steeper change ratio (inclination) of the slant zone. This brings about a higher sensitivity. However, since the half band width becomes narrower, the detection range, i.e., the dynamic range becomes smaller.

On the other hand, because the reflectance of the transmission/reflection part 3 changes in a different wavelength band, the reflection property for the detecting part 1 as a whole varies as in the slant zone R2 and the slant zone R3 as shown in FIG. 7. Therefore, by using light having a plurality of different wavelengths $\lambda_1'$, $\lambda_2'$ and $\lambda_3'$ in a single Fabry-Perot resonator, detection within a plurality of measuring ranges with different detection sensitivities and different dynamic ranges can be simultaneously carried out. It is therefore possible to achieve detection simultaneously with high detection sensitivity and a wide dynamic range.

According to this embodiment, the ultrasonic sensors 21 are used in an array. Therefore, ultrasonic scanning, deflection and convergence in the object body can be dynamically carried out in parallel for the ultrasonic sensors, and easily collect three-dimensional data about the object body. Since fine optical fibers are used in the detecting part and the derivation lines of signals (reflected light) from the detecting part, it is possible to use detection elements in a highly integrated array without leading to an increase of impedance in signal transfer.

According to this embodiment, furthermore, detection light containing a plurality of different wavelength components can be emitted from a plurality of single wavelength lasers having different wavelengths. In this case, light output is concentrated within a narrow wavelength range. It is therefore possible to improve an SN ratio in optical detection and achieve a higher detection sensitivity.

Figure 8:
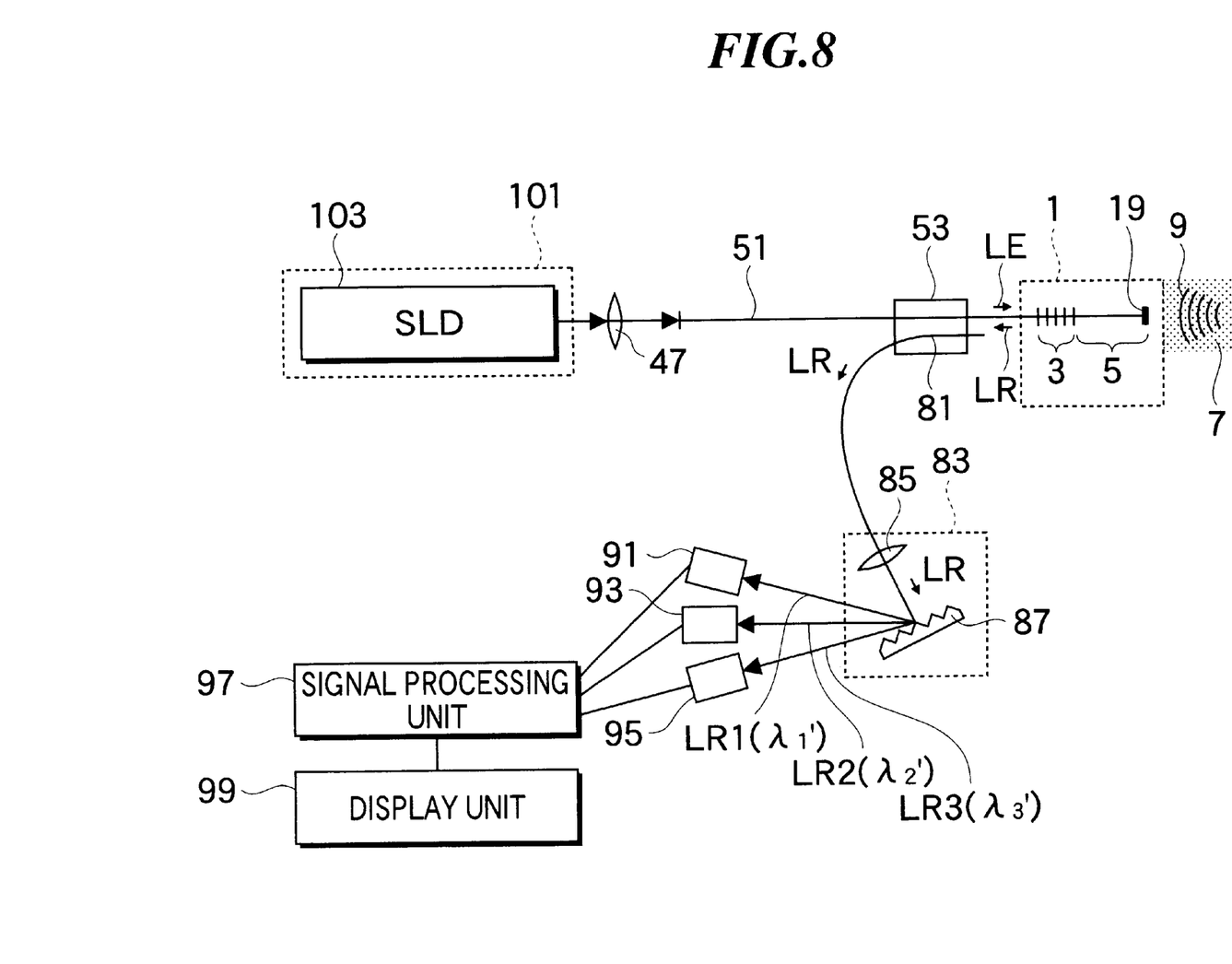
FIG. 8 illustrates a configuration of a dynamic change detecting apparatus according to a second embodiment of the invention, having a super luminescent diode (SLD) as a light source.

FIG. 8 illustrates the configuration of a dynamic change detecting apparatus according to a second embodiment of the invention. In this dynamic change detecting apparatus, a light source having a wide-band wavelength range, such as a light source unit 100 containing a super luminescent diode (SLD) 101 is used. The other configuration is the same as that shown in FIG. 2. According to this embodiment, this configuration permits emission of a detection light containing a plurality of different wavelength components from a light source having wavelengths within a wide band such as a super luminescent diode (SLD). In this case, there is available an advantage of a simple configuration of the light source.

Figure 9:
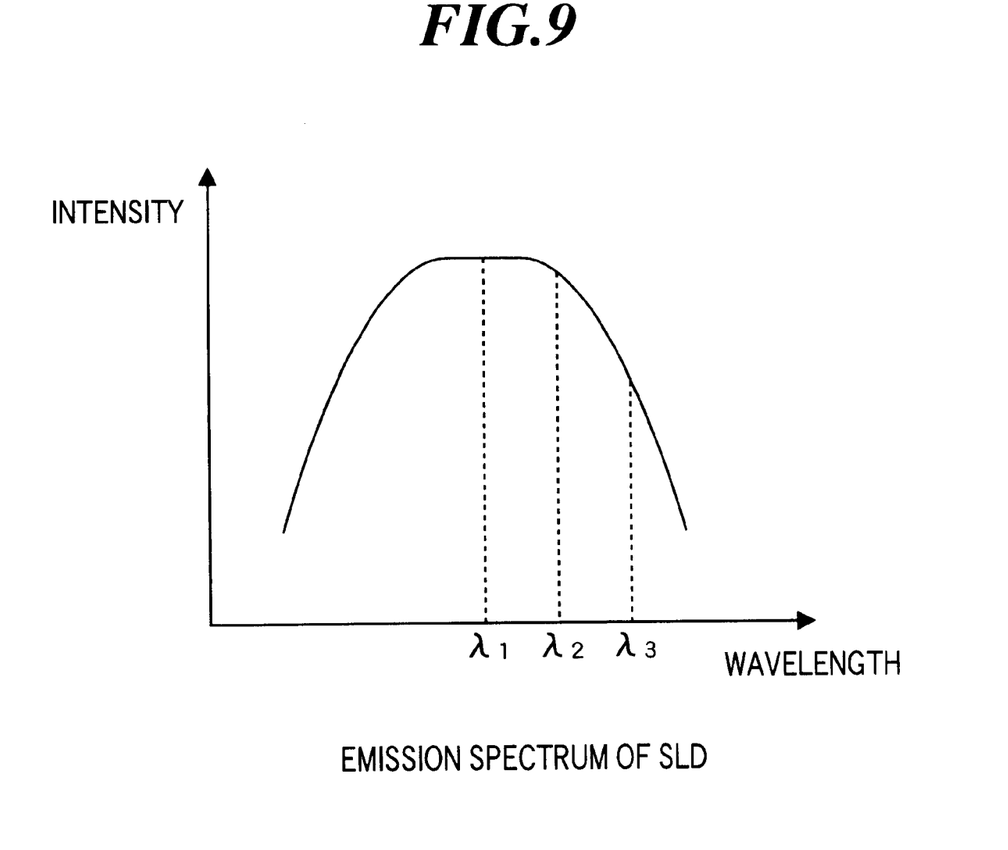
FIG. 9 illustrates the light emission property of SLD.

FIG. 9 illustrates emission property of an SLD: the vertical axis represents the emission intensity, and the horizontal axis represents the wavelength.

The light emitted from the SLD has a wide emission wavelength range (half band width: 20 nm to 30 nm) as shown in FIG. 9. Since this light is reflected by a Fabry-Perot resonator having the properties as shown in FIG. 7, a light having a spectral property which is a combination of the slant zones R1, R2 and R3 shown in FIG. 7, enters the wavelength separating unit 83 via an optical coupler. In the wavelength separating unit 83, only the components having the wavelengths $\lambda_1'$, $\lambda_2'$ and $\lambda_3'$ in the characteristic changing regions of the slant zones R1, R2 and R3 of FIG. 7 are selectively separated, respectively. Therefore, change of intensity of the light having respective wavelength components occurs on the basis of change in Fabry-Perot reflectance caused by incidence of an ultrasonic wave. An advantage similar to that in the first embodiment is thus available.

Figure 10:
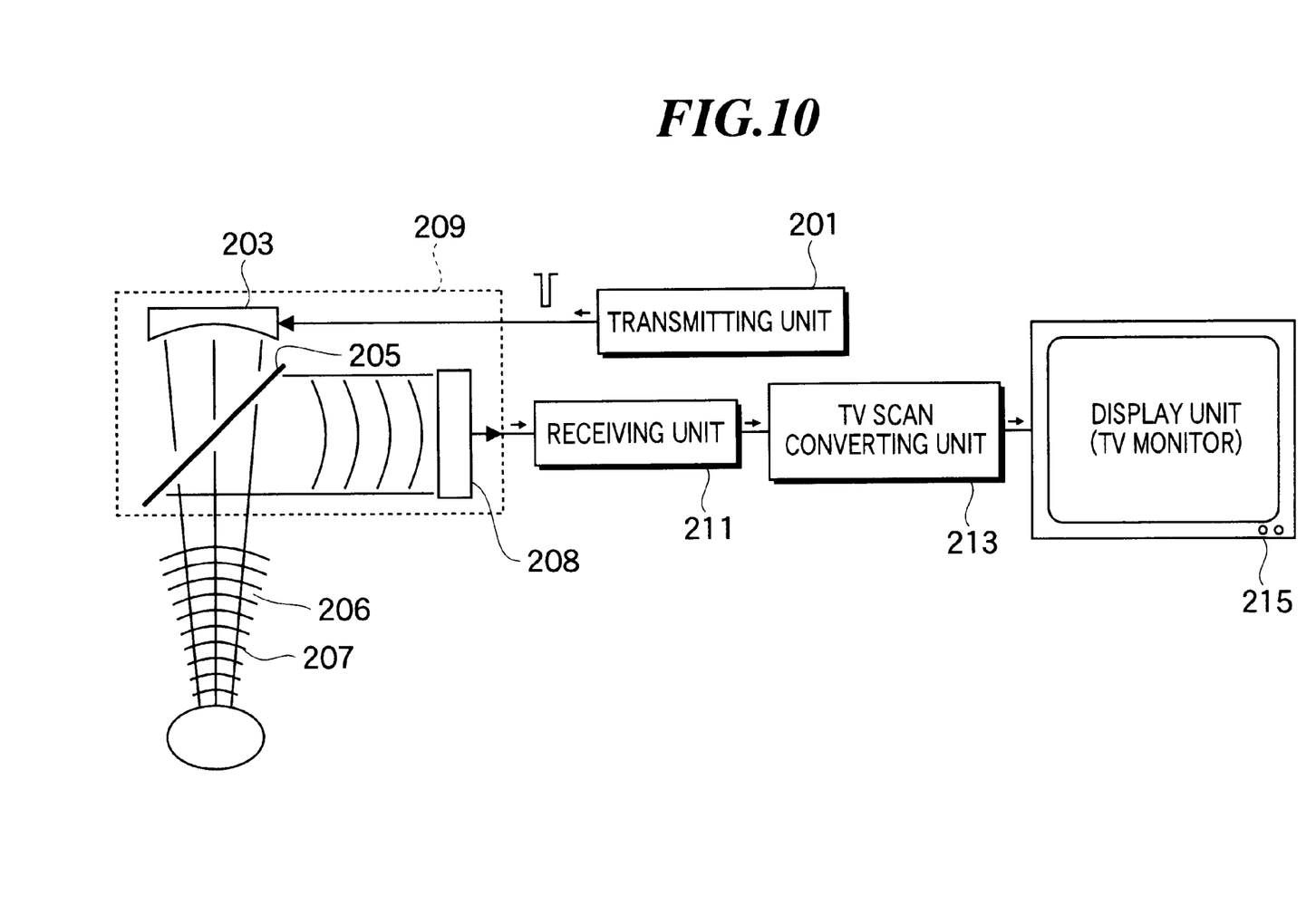
FIG. 10 is a block diagram showing a whole configuration of the ultrasonic diagnostic apparatus according to an embodiment of the invention.

FIG. 10 is a block diagram showing an entire configuration of an ultrasonic diagnostic apparatus according to an embodiment of the invention.

This ultrasonic diagnostic apparatus includes a transmitting unit 201, a probe 209, a receiving unit 211, a TV scan converting unit 213, and a display unit (TV monitor) 215.

The transmitting unit 201 sends a pulse-shaped drive signal to an ultrasonic transmitting transducer 203 using PZT or PVDF. The transducer 203 emits a ultrasonic wave, and enters the ultrasonic wave into an object 206.

In FIG. 10, a half mirror 205 for ultrasonic waves (such as a resinous sheet) is arranged below the transducer 203. In the object body 206, an ultrasonic echo 207 is reflected upward, and the ultrasonic echo is reflected to the right-hand by the half mirror 205 for ultrasonic waves, and enters a two-dimensional array ultrasonic detection element 208. This detection element 208 converts the ultrasonic wave into light and sends the light to a receiving unit 211. The receiving unit 211 converts an optical signal from the detection element 208 into an electric signal. A TV scan converting unit 213 conducts amplification and so on of the signal from the receiving unit 211, and then carries out an imaging processing. The imaged signal is sent to the display unit (monitor display) 215, and an image is displayed on the display unit 215.

The embodiments of the present invention have been described with reference to the drawings. The invention is not however limited to these embodiments, but various modifications and additions may be made. In the above description, ultrasonic wave propagating through an object body has been taken up as a dynamic change to be detected. Apart from this, it is also possible to detect dynamic changes such as changes in sound wave, acceleration, distortion, temperature and displacement.

According to the present invention, as described above, it is possible to select a combining condition of various detection sensitivities and dynamic ranges when detecting a dynamic change, or detect dynamic changes in parallel under a plurality of conditions.

What is claimed is:

1. A dynamic change detecting method comprising the steps of:
   (a) entering light having at least one wavelength component from one end of a transmission/reflection part having transmission/reflection properties varying with a wavelength of incident light into a detecting element having a detecting part composed by connecting a resonant part including a medium having a predetermined thickness and a total reflection mirror to the other end of the transmission/reflection part;
   (b) detecting the reflected light by means of said detecting part to obtain a detection signal; and
   (c) detecting dynamic change propagating to said total reflection mirror, on the basis of change in amplitude of the detection signal corresponding to change in size of said detecting part caused by propagation of the dynamic change.

2. A dynamic change detecting method according to claim 1, wherein:
   step (a) includes entering light having a plurality of different wavelength components into said detecting element;
   step (b) includes detecting the light reflected by said detecting part by separating said plurality of different wavelength components to obtain a plurality of detection signals; and
   step (c) includes detecting dynamic change propagating to said total reflection mirror at a plurality of different detecting sensitivities in parallel, on the basis of said plurality of detection signals.

3. A dynamic change detecting method according to claim 2, wherein step (c) includes detecting dynamic change propagating to said total reflection mirror at a plurality of different detecting sensitivities in parallel by using a plurality of slant zones having different half band widths of reflectance curves of said detecting part.

4. A dynamic change detecting method according to claim 1, wherein said transmission/reflection part includes an optical fiber Bragg grating.

5. A dynamic change detecting method according to claim 1, wherein said dynamic change includes an ultrasonic wave propagating through an object.

6. A dynamic change detecting method according to claim 1, wherein:
   step (a) includes entering light having at least one wavelength component into a plurality of detecting elements composing any one of a one-dimensional array and a two-dimensional array;
   step (b) includes obtaining a plurality of detection signals by detecting the light reflected by said detecting part of said plurality of detecting elements; and
   step (c) includes detecting dynamic change propagating to said total reflection mirror of said plurality of detecting elements, on the basis of change in amplitude of said plurality of detection signals.

7. A dynamic change detecting method according to claim 2, wherein step (a) includes entering light having a plurality of different wavelength components into said detecting element by using a plurality of single-wavelength lasers.

8. A dynamic change detecting method according to claim 2, wherein step (a) includes entering light having a plurality of different wavelength components into said detecting part, by using a light source having a wide-band light emission wavelength.

9. A dynamic change detecting methods according to claim 8, wherein said light source is a super luminescent diode (SLD).

10. A dynamic change detecting apparatus comprising:
a light source for emitting a light having at least one wavelength component;
a detecting element having a detecting part composed by connecting a resonant part including a medium having a predetermined thickness and a total reflection mirror to one end of a transmission/reflection part having transmission/reflection properties varying with a wavelength of incident light, light emitted by said light source being entered from the other end of said transmission/reflection part into said detecting element;
a plurality of light detectors for detecting the light reflected by said detecting part to detect a detection signal; and
a signal processing unit for detecting dynamic change propagating to said total reflection mirror, on the basis of change in amplitude of the detection signal corresponding to change in size of said detecting part caused by propagation of the dynamic change.

11. A dynamic change detecting apparatus according to claim 10, further comprising:
a light separating unit for separating the light reflected by said detecting part into a plurality of different wavelength components; wherein:
said light source emits light having said plurality of different wavelength components;
said plurality of light detectors detect the light divided by said light separating unit respectively to obtain a plurality of detection signals; and
said signal processing unit detects dynamic change propagating to said total reflection mirrors of said plurality of detecting elements, on the basis of change in amplitude of said plurality of detection signals.

12. A dynamic change detecting apparatus according to claim 11, wherein:
said signal processing unit detects dynamic change propagating to said total reflection mirrors at a plurality of different sensitivities in parallel by using a plurality of slant zones having different half band widths of reflectance property curve of said detecting part.

13. A dynamic change detecting apparatus according to claim 10, wherein said transmission/reflection part comprises an optical fiber Bragg grating.

14. A dynamic change detecting apparatus according to claim 10, wherein said dynamic change is an ultrasonic wave propagating through an object.

15. A dynamic change detecting apparatus according to claim 11, further comprising:

a plurality of detecting elements composing any one of a one-dimensional array and a two-dimensional array; wherein:
said plurality of light detectors detects the light reflected by said detecting part of said plurality of detection signals to obtain a plurality of detection signals; and
said signal processing unit detects dynamic change propagating to said total reflection mirrors of said plurality of detecting elements, on the basis of change in amplitude of said plurality of detection signals.

16. A dynamic change detecting apparatus according to claim 11, wherein said light source includes a plurality of single-wavelength lasers emitting the light having a plurality of different wavelength components, respectively.

17. A dynamic change detecting apparatus according to claim 11, wherein said light source includes a light source having a wide-band light emission wavelength.

18. A dynamic change detecting apparatus according to claim 17, wherein said light source is a super luminescent diode (SLD).

19. An ultrasonic diagnostic apparatus comprising:
a transmitting unit for transmitting an ultrasonic wave to an object;
a light source for emitting a light having at least one wavelength component;
a detecting element having a detecting part composed by connecting a resonant part including a medium having a predetermined thickness and a total reflection mirror to one end of a transmission/reflection part having different transmission/reflection properties in response to a wavelength of incident light, the light emitted by said light source being entered from the other end of said transmission/reflection part to said detecting element;
a plurality of light detectors for detecting the light reflected by said detecting part to obtain a detection signal;
a signal processing unit for detecting dynamic change propagating to said total reflection mirror, on the basis of change in amplitude of the detection signal corresponding to change in size of said detecting part caused by propagation of the dynamic change; and
an image display unit for displaying an image on the basis of the signal output from said signal processing unit.

20. An ultrasonic diagnostic apparatus according to claim 19, further comprising:
a light separating unit for separating the light reflected by said detecting part into a plurality of different wavelength components; wherein:
said light source emits light having a plurality of different wavelength components;
said plurality of light detectors obtain a plurality of detection signals by detecting the light separated by said light separating unit; and
said signal processing unit detects dynamic change propagating to said total reflection mirror of said plurality of detecting elements, on the basis of change in amplitude of said plurality of detection signals.

* * * * *